(12) United States Patent
Giniger et al.

(10) Patent No.: US 9,358,193 B2
(45) Date of Patent: Jun. 7, 2016

(54) WHITENING COMPOSITIONS AND METHODS INVOLVING NITROGEN OXIDE RADICALS

(76) Inventors: Martin S. Giniger, New York, NY (US); Matthew S. Spaid, New York, NY (US)

( * ) Notice: Subject to any disclaimer, the term of this patent is extended or adjusted under 35 U.S.C. 154(b) by 1366 days.

(21) Appl. No.: 11/355,501

(22) Filed: Feb. 15, 2006

(65) Prior Publication Data

US 2006/0198796 A1    Sep. 7, 2006

Related U.S. Application Data

(60) Provisional application No. 60/653,421, filed on Feb. 15, 2005, provisional application No. 60/734,549, filed on Nov. 7, 2005, provisional application No. 60/734,523, filed on Nov. 7, 2005.

(51) Int. Cl.
| | |
|---|---|
| *A61K 8/20* | (2006.01) |
| *A61K 8/22* | (2006.01) |
| *A61K 8/365* | (2006.01) |
| *A61K 8/04* | (2006.01) |
| *A61K 8/19* | (2006.01) |
| *A61K 8/38* | (2006.01) |
| *A61Q 11/00* | (2006.01) |
| *A61Q 19/02* | (2006.01) |

(52) U.S. Cl.
CPC ........... *A61K 8/365* (2013.01); *A61K 8/046* (2013.01); *A61K 8/19* (2013.01); *A61K 8/38* (2013.01); *A61Q 11/00* (2013.01); *A61Q 19/02* (2013.01); *A61K 2800/222* (2013.01); *A61K 2800/88* (2013.01)

(58) Field of Classification Search
USPC ........................................... 424/718
See application file for complete search history.

(56) References Cited

U.S. PATENT DOCUMENTS

| | | | | |
|---|---|---|---|---|
| 4,425,322 | A * | 1/1984 | Harvey et al. | 424/52 |
| 5,670,177 | A * | 9/1997 | Briend et al. | 424/718 |
| 6,280,708 | B1 * | 8/2001 | Ryles et al. | 424/53 |
| 6,475,472 | B2 * | 11/2002 | Joiner et al. | 424/53 |
| 6,746,664 | B2 * | 6/2004 | Allred | 424/53 |
| 2003/0175362 | A1 * | 9/2003 | Kross et al. | 424/718 |
| 2004/0071772 | A1 * | 4/2004 | Narita et al. | 424/465 |

FOREIGN PATENT DOCUMENTS

| | | | | |
|---|---|---|---|---|
| GB | 2354441 | * | 3/2001 | A61K 7/16 |
| WO | WO98/46195 | * | 10/1998 | A61K 6/00 |

\* cited by examiner

*Primary Examiner* — Walter Webb
(74) *Attorney, Agent, or Firm* — Peter B. Scull; Hamilton, DeSanctis & Cha LLP

(57) ABSTRACT

A tissue treatment composition comprising an effective amount of a nitric oxide, nitroxyl or nitrogen oxide composition for color effect of the tissue.

7 Claims, 3 Drawing Sheets

FIGURE 1. DUAL BARREL SYRINGE WITH MIXING TIP
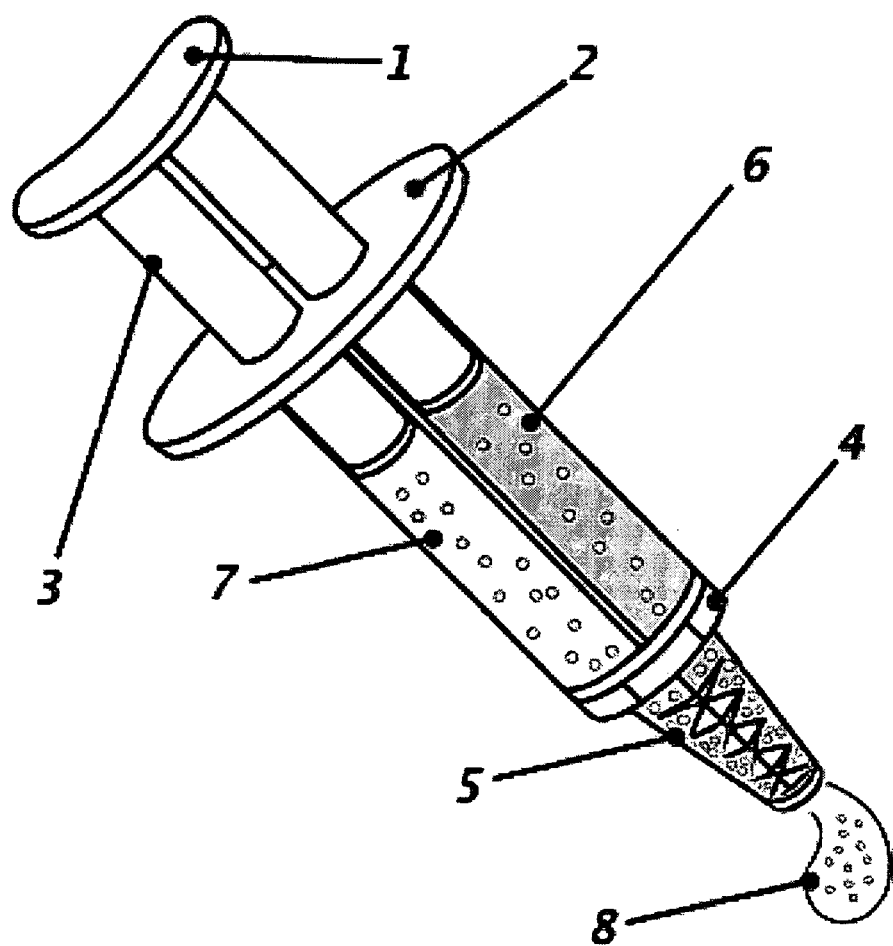

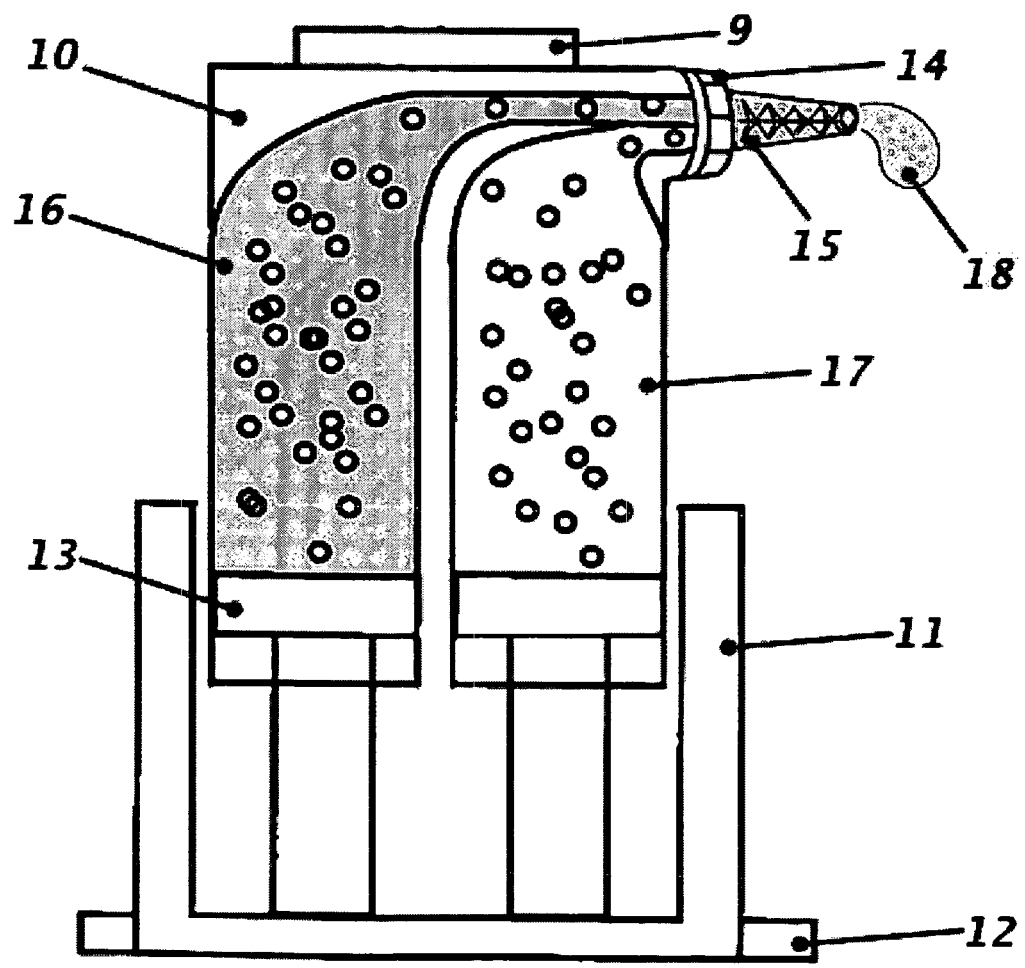
FIGURE 2. PUMP WITH MIXING TIP

FIGURE 3. PUMP WITH FLIP TOP CLOSURE
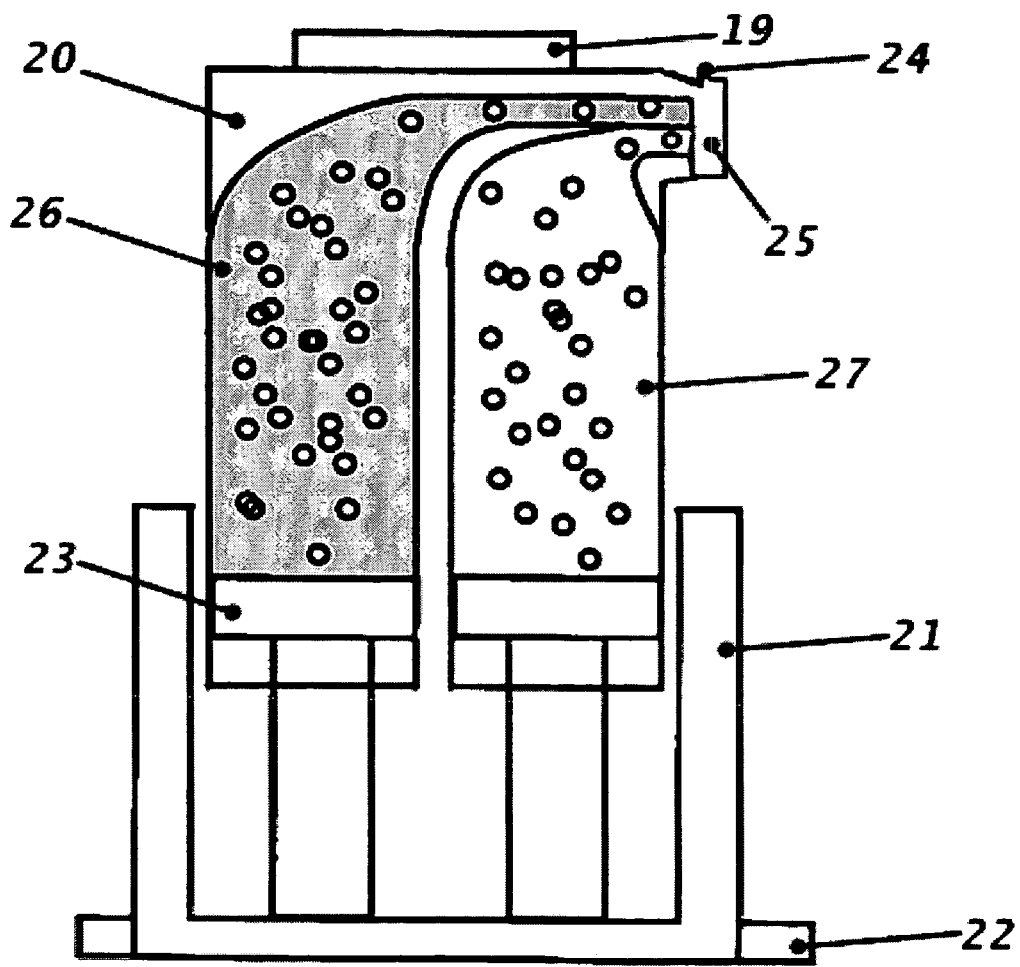

WHITENING COMPOSITIONS AND METHODS INVOLVING NITROGEN OXIDE RADICALS

CROSS-REFERENCE TO RELATED APPLICATIONS

The present invention claims the benefit of and priority from the prior-filed U.S. Provisional Patent Application No. 60/653,421; filed Feb. 15, 2005, entitled "Whitening System Capable of Delivering Effective Whitening Action"; and No. 60/734,549; filed Nov. 7, 2005, entitled "Oral Care Compositions and Methods"; and No. 60/734,523 filed Nov. 7, 2005, entitled "Tooth Whitening Compositions and Methods Involving Nitrogen Oxide Radicals"; the subject matter of each of which hereby being specifically incorporated herein by reference for all that they disclose and teach.

BACKGROUND

This invention relates to improvements in whitening compositions and methods of using same. In particular, the invention provides whitening compositions and methods that use free radicals of nitrogen oxide and/or nitric oxide and/or other nitroxyls to achieve a faster and improved level of whitening.

As a background on whitening generally, and more particularly on tooth whitening, it may first be noted that a tooth is comprised of an inner dentin layer and an outer hard enamel layer that is the protective layer of the tooth. The enamel layer of a tooth is naturally an opaque white or slightly off-white color. It is this enamel layer that can typically become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a pellicle film on the teeth. These staining and discoloring substances can then permeate the enamel layer. This problem occurs gradually over many years, but imparts a noticeable discoloration of the enamel of one's teeth.

There are available to dentists and consumers many different oral compositions for home and professional in-office use which contain 1-45% by weight concentrations of a peroxygen compound such as hydrogen peroxide which when applied on the teeth may effect whitening of stains. These compositions all require different amounts of time to achieve a tooth whitening effect. These times range from 90 to 120 minutes for a dentist applied, light-activated whitening system to two weeks or more of over night exposure for tray-delivered whitening products. Currently even the top selling brands of dentist-applied, chair-side tooth whitening systems require a minimum of three (3) twenty-minute applications and an overall minimum of ninety (90) minutes or more to complete when all manufacturers' instructions are followed.

Among the chemical strategies available for removing or destroying tooth stains, the most effective compositions contain an oxidizing agent, usually a peroxygen compound such as hydrogen peroxide, in order to attack the chromogen molecules in such a way as to render them colorless, water-soluble, or both. In one of the most popular approaches to whitening a patient's teeth, a dental professional will construct a custom-made tooth-whitening tray for the patient from an impression made of the patient's dentition and prescribe the use of an oxidizing gel to be dispensed into the tooth-whitening tray and worn intermittently over a period of time ranging from about 2 weeks to about 6 months, depending upon the severity of tooth staining. These oxidizing compositions, usually packaged in small plastic syringes, are dispensed directly by the patient, into the custom-made tooth-whitening tray, held in place in the mouth for contact times of greater than about 60 minutes, and sometimes as long as 8 to 12 hours. The slow rate of whitening is in large part the consequence of the very nature of formulations that are developed to maintain stability of the oxidizing composition.

Alternatively, there are oxidizing compositions (generally those with relatively high concentrations of oxidizers) which are applied directly to the tooth surface of a patient in a dental office setting under the supervision of a dentist or dental hygienist. Theoretically, such tooth whitening strategies have the advantage of yielding faster results and better overall patient satisfaction.

Oral compositions for whitening teeth have also been available containing peracetic acid dissolved or suspended in a vehicle. The peracetic acid may have been generated within a dentifrice vehicle by combining water, acetylsalicylic acid and a water soluble alkali metal percarbonate.

Formulations for oxygen liberating compositions for the whitening of teeth have also been used in either anhydrous or hydrated pastes or gels. Hydrated examples include an aqueous oral gel composition including about 0.5 to about 10% by weight urea peroxide and 0.01 to 2% by weight of a fluoride providing compound, and/or a water containing a hydrogen peroxide-Pluronic thickened oral gel composition.

Another example includes a toothpaste containing a combination of calcium peroxide and sodium perborate oxidizing agents, dicalcium phosphate, calcium carbonate and magnesium carbonate cleaning agents, sorbitol humectant, cornstarch and cellulose gum thickening agents, and an anionic detergent. Other examples include oral compositions containing peroxyacids and alkyl diperoxy acids having alkylene groups containing 5-11 carbon atoms for removing stains from teeth.

The prolonged period needed for effective whitening may be undesirably time-consuming. Thus, any whitening system that can potentially reduce the time factor is preferable. To accomplish this in the present invention, it has been recognized that nitrogen-containing free radicals and various related nitroxyl-based free radicals are more reactive than the oxygen singlet free radicals that are generated by all previously described tooth whitening compositions. The present invention then makes use of the release of free radicals containing nitrogen to effect a more rapid whitening of the teeth.

First, some background information on nitrogen oxide (NO) will be presented. NO is one of the oldest molecules on earth, being formed in the primitive atmosphere of the cooling planet. Until recently, NO had been regarded almost solely as a predominantly harmful product, being the cause of, for example, acid rain and atmospheric pollution. However in 1987, NO was discovered to be the chemical responsible for the actions of endothelial derived relaxing factor. Following this finding, NO research has expanded exponentially, and it is now regarded by many in the scientific community as one of the greatest discoveries of the 20th century. In recognition of this, two Nobel prizes have been awarded to researchers in the NO field, and it was named as molecule of the year by the scientific journal, *Science*, in 1998.

NO is a small gaseous molecule with chemical properties that make it uniquely suitable as both an intra- and inter-cellular messenger. Because it possesses an unpaired electron, NO reacts with other molecules with unpaired electrons, including colored organic molecules known as chromogens.

As a neutral gaseous molecule, NO can diffuse over several cell lengths from its source to exert control over certain enzymes and regulate key cellular functions. Also, because of its reactivity, NO has been used as an effector molecule to kill tumors and pathogens. The combined properties of its ability to regulate enzymes across long distances as well as its high, reactivity with other molecules give NO its unique dual role as both a powerful signaling molecule and lethal effector molecule.

Because of these powerful functions, the production of this pivotal mediator is tightly regulated and there is ample literature to show that too little or too much NO production contributes to numerous human diseases and disorders. Decreased NO generation in the penis, for example, results in impotence. Decreased NO generation is also thought to have a role in hypertension.

Nitric oxides are known to be as much as five or more times more reactive than oxygen free radicals. This is based on research that shows that oxyhemoglobin binds NO faster by five to six orders of magnitude than oxygen.

It is estimated the half-life of NO free radical is close to five seconds. Even though short, it is of quite sufficient length to allow diffusion between enamel rods and over the enamel surface as prior research has shown that in five seconds the NO radical can diffuse many human lung cell diameters and enable it to function as a transcellular messenger. Research has shown that NO may diffuse the entire length of a cell (~0.11 m) within a millisecond. Therefore the rate of travel within biological systems can be calculated to be 1 mm per second. Human tooth enamel is 2-3 mm thick; hence the 5 second half-life if NO is more than sufficient time for the free radical to travel to the entire depth of an enamel rod.

Research interest of NO in dentistry has been relatively recent, and only a small minority of the 50,000 papers currently cited on NO have been concerned with the oral sciences, although dentistry's interest in NO is expanding rapidly. Of greatest interest has been the role of NO in the pathogenesis and prevention of periodontal disease and in the biology of oral cancer.

The chemistry of NO reveals that its arrangement of one atom of nitrogen and one of oxygen leaves an unpaired electron, which makes the molecule a highly reactive free radical. The result is a molecule with special properties which, as described below, make it a previously-unrecognized ideal tooth whitening agent.

One of the primary advantages of NO over the superoxide free radical (the predominant species liberated in tooth whitening preparations containing hydrogen peroxide), is that NO has a low propensity to react with itself at physiological temperatures to form a nitrogen gas bubble. Contrarily, superoxide free radicals do react with themselves at an efficiency of 99.99% combining to form an oxygen bubble, and thus cause its efficiency at removing the color from chromophoric stains on teeth to be very low. It is for this reason that in nature, the NO free radical is 10 to 100 times more efficient in whitening organic matter. As a result, because NO does not readily combine with itself to form a stable molecule, and also because it is a very reactive free radical, it has been recognized hereby that NO should be far more efficient than the superoxide free radical at whitening teeth. The superiority of the NO radical has also hereby been confirmed clinically.

Of particular importance for the formulation of a tooth whitening compositions is that NO– does not remain as a nitrogen oxide free radical moiety in aqueous solution. Instead, NO quickly yields nitrite ($NO_2$—) and nitrate ($NO_3$—) as end products in an aqueous environment. Therefore it is ultimately the FDA-approved nitrite or nitrate end product of Nitrogen radical-water chemistry that would be used as the predominant entity for the chromogen oxidizers in the aqueous whitening products described hereinbelow. Both the nitrate and nitrite end products possess an unpaired electron making it a reactive paramagnetic moiety which, as recognized here, is capable of rapidly interacting with organic stain molecules (chromogens) which contain carbon-carbon bonds filled with two electrons.

It may also be noted that in non-aqueous environments, it is possible that some NO– radicals may react rapidly with the superoxide radicals (typically found in tooth whitening chemistry), forming highly reactive peroxynitrite anions (ONOO—). However, the aqueous nature of the present invention precludes formation of these anions in significant amounts.

Another noteworthy outcome of nitrogen oxide whitening is that very small amounts of nitrosonium cations (NO+) and nitroxyl anions (NO–) will be formed in aqueous environments. At low concentrations these will not be biological systems, but because of their extremely high reactivity, it has been recognized hereby that they can interact with tooth surface chromogens in a more efficient manner than could either the hydroxyl or superoxide free radical.

Regarding their safety; Nitrite and Nitrate salts are typically supplied as white rhombic crystals. They are easily soluble in water and have strong gyroscopicity. These have typically been used in the food and fabric industries as bleaching agents, corrosion inhibitors, antitoxic and analytical agents. Daily exposure to Nitrites has been cautioned by the FDA (for example when used as a color fixative for meats); however it is also credited with significantly reducing the botulism risk in humans and is thus found commonly. It is also commonly used in pharmaceuticals; photographic and analytical reagents. Furthermore and even though safe, the compositions presented here are, according to conventional standards, not intended for daily use, but rather for a prescribed treatment time that in typical situations should perhaps not be repeated more than twice yearly (though more often may be practiced, as understood, and perhaps prescribed by a physician). Even further, the compositions hereof are not intended for consumption, but rather only intended for the topical applications described, as on the teeth in the primary examples.

Presented hereafter is background information on activating bleaching agents with light energy. Scientists have identified many kinds of ultraviolet (UV) photoactivators, which are capable of working in nature to reduce the color of chromophoric stains. These include: transition metal complexes, keto acids, riboflavin, pteridines, algal pigments, cyanocobalamine, thiamin, biotin and aromatic ketones. The pathways by which photo-bleaching can theoretically occur on tooth surfaces are of two types. First, if the absorption spectrum of the colored chromogen overlaps with the spectrum of incoming radiation, the substrate may undergo photoreaction directly, e.g., the notion of fading color with light. Secondly, and a likely more powerful explanation; UV energy may be absorbed by photo activators that then react with the tooth surface chromogens, resulting in an "indirect" photobleaching.

Indirect photobleaching is mediated by transient species (free radicals) that are rapidly consumed by subsequent reactions. For these mechanisms, the rate of reaction is determined by the quantity and type of chromogen, activator, free radicals and incoming UV radiation. Surface gradients involving any of these factors will lead to altered rates of photobleaching at the enamel/bleaching agent interface.

In nature, the major photochemical intermediate free radicals include singlet oxygen, O.; superoxide $O_2$—; hydroperoxide $HO_2$; and various other peroxy radicals, $RO_2$. These have previously been described for the purpose of bleaching teeth.

Singlet oxygen free radicals, O. (the most common type of free radical liberated from hydrogen peroxide in the presence of light, heat or other activators), are formed primarily through energy transfer from the excited triplet states of dioxygen, $3O_2$. (as seen in the case of hydrogen peroxide), and wavelengths in the UV-A (315-400 nm) and UV-B (280-315 nm) spectra have been shown to be most effective in their formation. Quantum yields (the fraction or percentage of absorbed photons which give rise to products) range from 1-3% and generally decrease with increasing wavelength. Because the high concentrations of hydrogen peroxide or similar compounds are present in tooth bleaching preparations, its decay into water and O. is dominated by this pathway when UV light/activator systems are used in professional tooth bleaching formulas.

The exact mechanism of how these singlet oxygen free radicals come to be formed still remains unclear. Some researchers have suggested that O. is formed by direct electron transfer from the excited triplet states to $O_2$. However, reduction of $O_2$ by radicals or radical ions produced by intramolecular electron transfer reactions, H-atom abstractions and/or homolytic bond cleavages, is equally, if not more plausible. It is also known that transition metal complexes having one-electron reduction potentials falling between the $O_2/O_2$— and $O_2$—/$HO_2O_2$ couples can rapidly catalyze O. free radical formation.

Even so, knowing that tooth bleaching formulations rely on the singlet oxygen O. free radical, the universe and the earth's natural environment takes a broader and more efficient approach to photobleaching. For example, it is known that in the oceans of the earth, there are other important photochemical radicals that work as intermediates in combination with bacterial hydrogen peroxide and are mostly responsible for photobleaching of coral reefs. These more efficient photobleaching reactions use NO– (nitrogen oxide) and $NO_3$— & $NO_2$— (nitrate/nitrite) radicals. Nitroxyl radical photobleaching chemistry (as described in depth by several researchers) may be initiated by UV from sunlight reacting with NO–, $NO_3$— & $NO_2$— (nitrate/nitrite) radicals.

Evidence for the photobleaching ability of nitrogen oxide radicals has been acquired by employing stable nitroxide radicals to trap the carbonate radicals, the immediate precursors to the reduced chromogen. Using a highly-sensitive fluorescence detection scheme combined with high performance liquid chromatography, a number of molecular fluorescent-tagged OH— and carbonate radicals have been detected in seawater and combined with high molecular weight chromophores. Note, just as important in nature are the highly reactive hydroxyl radicals, OH—, which again are much more reactive than singlet oxygen free radicals and are produced primarily through the photolysis of nitroxyl radicals. In this case, $NO_2$— is known to react with UV light and peroxide formed by ocean bacteria and plankton to form the OH— radical. The OH— then reacts with an available carbon source producing carbonate radicals. The carbonate radical may then self-terminate in competition with its oxidation of organic chromogens into less colored molecules. The photolysis of Nitrate is also important. $NO_3$— reacts with UV light and plankton $H_2O_2$ to generate OH— as well as $NO_2$—. Subsequent reactions of $NO_2$ can produce $NO_3$— thereby coupling the dynamic cycles of $NO_2$— and $NO_3$— photobleaching.

Therefore the oxidation of the nitrogen oxide, nitrate and nitrite is very similar to photo-fenton reaction in which reduced metals such as Fe(II) react with $H_2O_2$ and UV light to produce a single OH— radical. However using nitrogen oxides in the oxidation process instead of hydrogen peroxide is much more powerful. This is because hydroxyl moieties are generated with less UV activation energy thus giving NO containing tooth whiteners the capability of producing more reduction in chromophoric tooth stain in a given period of time or for a given level of UV energy (the high quantum yield for this reaction is 98%).

SUMMARY

Because there is thus a need for improved compositions for whitening teeth that overcome the limitations of the prior art described above, and because there is a need for tooth whitening compositions and methods capable of whitening teeth quickly and safely, without harm to tooth enamel, dentin, or pulp, the compositions and methods of the present invention described herein have been designed to satisfy these and other needs.

The present invention offers the advantages that active NO radicals are generated quickly, in large quantities and are more reactive than singlet oxygen free radicals for the purpose of bleaching organic materials, thereby facilitating convenient and effective use by the consumer as well as professional use by the dentist.

It is therefore an aspect of this invention to provide relatively faster and/or safe tooth whitening compositions and methods. Similarly, it is a further aspect of this invention to provide a tooth whitening composition that shortens the treatment time required to obtain a given level of tooth whitening that is more satisfactory to both the patient and the dentist. Ultimately, in many embodiments, a nitroxyl or nitrogen oxide whitening composition hereof may be capable of delivering more efficient whitening action.

A further aspect may be in the use of novel chemistry to whiten teeth even though similar chemical reactions have been described in the scientific literature as causing the whitening of coral reefs, fabrics and/or foods. The present invention describes compositions which may be supplied in two parts, and when combined cause a chemical reaction that yields chemical radicals for the bleaching of teeth. These radicals have been proven in nature to whiten more profoundly and more rapidly than the radicals derived from per-oxygen-based whitening or bleaching techniques, including those using hydrogen peroxide, carbamide peroxide, calcium peroxide, sodium perborate or any other similar compound.

The current invention describes the use of NO radicals (e.g., nitrogen oxide free radicals and nitrate and/or nitrite ions) with and/or without the use of UV light for the purpose of reducing enamel chromophores into less colored and/or colorless moieties, essentially leaving teeth whiter and brighter in a very rapid manner. The nitroxyls and particularly the nitroxyl radicals that are of primary preferred relevance for tooth whitening or bleaching herein include elemental nitrogen in five oxidation states (NOx: $N_2O$, NO., $NO_2$—, $NO_2$., $NO_3$—). Thus, as used herein, the terms nitroxyl radical or nitrogen oxide free radical (NO) includes these five oxidation states of nitrogen (NOx: $N_2O$, NO., $NO_2$—, $NO_2$., $NO_3$—). Even so, the broader chemistry hereof also may make use of an array of interrelated redox forms implicated in the biochemistry of dioxygen: e.g., nitrosonium cation (NO+) and nitroxyl anion (NO–). Still more broadly as used herein, a nitroxyl compound may be any molecule that contains a terminal group of nitrogen and oxygen.

In discrete embodiments hereof, a tooth whitening nitroxyl composition may be provided in a single phase or multiple phase forms. In multiple phase forms, the composition can be either a two-component system involving two initially isolated but combinable components or a one-compartment multi-phase system.

In an embodiment, the composition hereof may be foamable or otherwise operable or at least partially operable as a foam.

In other embodiments, a one- or two-component composition may be provided which is foamable composition; the two-component embodiments having a first component including at least one nitroxyl compound and a second component including at least one foaming agent; wherein the two components may be combined to form a foam.

Another embodiment may also include a two-component foamable composition including a first component having at least one nitroxyl compound in an aqueous solution; and a second component including at least one foaming agent in another form such as a solid form. This could be a powder/liquid two-component composition.

A still further embodiment may include a one-component, multi-phase, foamable composition, typically liquid, including at least one nitroxyl compound in an aqueous phase and at least one foaming agent in an oil phase, wherein the two phases are combinable to form a foam.

Still further, another embodiment may include an effervescent foaming one-component composition including at least one nitroxyl compound. The resultant foams hereof whether in one or two component forms may have a half life of from about 2 to about 60 minutes.

Other embodiments may include any one or two component composition having a first component including at least one nitroxyl compound in an aqueous solution and at least some amount of peroxide and peroxide stabilizer in the form of an ion scavenger; and a second component including at least one foaming agent or thickening agent and at least one effervescent agent and at least one nitroxyl and/or peroxide activator; wherein said activator may promote the rapid decomposition of the nitroxyl and/or peroxide compound and may also cause additional foaming action not related to any foaming agent added.

In some alternatives, the nitroxyl compound may be activated or accelerated by the use of reduced amounts of UV light energy. Such an embodiment may include a light-activatable nitroxyl composition having a first component including at least one nitroxyl compound and a second component including a lower oxidative state transition metal salt; wherein the two components may be combinable to form a foam or a type of tooth adherent gel.

Another embodiment may involve a method of tooth whitening including: providing a whitening composition in a one- or two-component system, the composition including at least one nitrogen oxide or nitroxyl compound; forming nitrogen oxide radicals from the at least one nitrogen oxide or nitroxyl compound; and, applying said whitening composition with the nitrogen oxide radicals on a tooth surface for whitening.

A method hereof may include the whitening composition being in the form of a foam or gel. One foaming method may include: providing a whitening composition in a two-component system, a first component may include at least one nitroxyl compound and a second component may include at least one foaming agent; and combining said first and second components to create a whitening foam.

Another method of tooth whitening may include: providing a whitening composition in a two-component system, a first component including at least one nitroxyl compound and a second component including at least one nitroxyl photoactivator and one foaming agent; and, combining said first and second components to create a whitening foam; and illuminating the foam with light.

In another aspect, a nitroxyl radical whitening composition may include ingredients capable of increasing the half life of the foam that is generated. Such a stabilizer may, for example, be added to facilitate the formation of a water-soluble, longer-lasting, collapsible foam structure.

In a further aspect, the first component of a nitroxyl radical whitening composition may include at least one source of calcium, strontium and/or mixtures thereof and the second component may include at least one source of phosphate.

In yet a further aspect, the first component of a nitroxyl radical whitening composition also may include a de-sensitizing agent.

In yet an additional aspect, a nitroxyl radical whitening composition may include a peroxide and/or a peroxide activator.

In yet another aspect, a two-component nitroxyl radical whitening composition may contain peroxide compounds in both components.

In yet still one further aspect, a nitroxyl radical whitening composition may include a foam stabilizer.

In yet an additional aspect, a nitroxyl radical whitening composition may contain a nitrogen oxide activator.

In yet an additional aspect, a nitroxyl radical whitening composition may contain at least one solvent suitable for solubilizing stains.

In still yet another aspect, a two-component nitroxyl radical whitening composition may be provided in a double-barrel syringe (see FIG. 1 and description thereof below).

In still yet a further aspect, a two-component nitroxyl composition may be provided in a double-barrel pumpable dispenser (see FIGS. 2 and 3 and descriptions thereof below). The pumpable dispenser can be provided with a metering device for varying the proportion of each component in the final foam. The metering device can be adjusted to produce ratios of the two components of about 10:1 to 1:10, inter alia.

In still yet a further aspect, a two-component nitroxyl composition may be provided in two separate ampoules, the contents of which can be manually combined with a paint brush in a suitable vessel. A 1:1 ratio or other ratio may be used.

The detailed description set forth herein below is intended as a description of a variety of exemplary tooth whitening or bleaching compositions provided in accordance with one or more aspects of the present invention and is not intended to represent the only forms which may be prepared or utilized. The description sets forth features and/or operations for preparing and using tooth whitening compositions according hereto. It is to be understood, however, that the same or equivalent functions and ingredients incorporated in the tooth whitening compositions hereof may be accomplished by different embodiments that are nevertheless also intended to be and are encompassed within the spirit and scope of the present invention.

DETAILED DESCRIPTION OF THE DRAWINGS

In the drawings:

FIG. 1 is a dual-chamber syringe useful for dispensing compositions hereof;

FIG. 2 is a dual-chamber dispenser useful for dispensing compositions hereof; and, FIG. 3 is another dual-chamber dispenser useful for dispensing compositions hereof.

DETAILED DESCRIPTION

In one of various preferred embodiments, the sources of nitroxyl free radicals may be weak nitric acid (0.2%-1.0%) and/or calcium nitrate (0.2% to 1.0%). A generalized, conceptual chemical reaction not unlike the following may take place with water to produce many fast and efficient NO and OH free radicals as well as slower oxygen (O$^-$) free radicals:

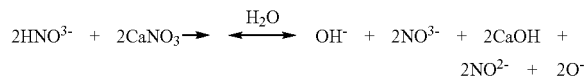

In another of various preferred embodiments, the sources of nitroxyl free radicals may be weak nitric acid (0.2%-1.0%) and/or calcium nitrate (0.2% to 1.0%). The following generalized chemical reactions may take place in the presence of a photoactivator transition metal, water and UV light to produce many fast and efficient NO and OH free radicals as well as slower oxygen free radicals:

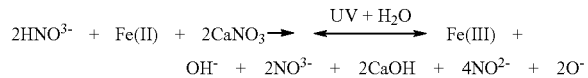

When Nitric Acid is used, it may typically be provided as a 10% aqueous solution. When used alone, the amount of the nitric acid aqueous solution in the first component may range from, for example, about 0.2% to about 1.0%. When Calcium Nitrate is desired to be used, nitric acid should also be present, and they should usually be added in similar proportions.

The result may be a nitroxyl or nitrogen oxide composition which involves the use of NO radicals which may be adapted for the purpose of reducing enamel chromophores into less colored and/or colorless moieties, essentially leaving teeth whiter and brighter in a very rapid manner.

The composition of the present invention can also include other active ingredients, such as nitroxyl activators, peroxide activators, effervescent agents, de-sensitizing agents, re-mineralizing agents, and fluoridating agents.

The addition of nitroxyl activators into the second component of a two component composition may have the capacity to also increase the photo-whitening efficiency of the peroxide compositions of the present invention. Suitable nitroxyl activators may include lower oxidative state transition metal salt. The metal salt may catalyze the whitening or bleaching action of the peroxide to produce faster effective whitening at lower peroxide concentrations. The preferred transition metals are those of lower atomic numbers including lower atomic number transition metals such as those ranging from atomic number 21 to 30. Also, those with lower oxidative states are also more preferred, including Iron(II), manganese(II), cobalt (II), copper(II) or mixtures thereof.

When used, only a very small amount of the transition metal salt is needed, for example, from about 0.01% by weight to about 4% by weight, or in a further example, from about 0.03% by weight to about 2% by weight, and for an even further example, from about 0.04% to about 1% by weight.

The nitroxyl activator can also include alkali salts such as potassium iodide, potassium chloride, sodium iodine, sodium chloride and combinations thereof.

Moreover, indeed, the composition also may include at least one peroxide component which, for example, may include metal ion free peroxide compounds. Examples of suitable metal ion free peroxide compounds include hydrogen peroxide and organic peroxides including urea peroxide (carbamide peroxide), salts of peroxides formed from the alkali and alkaline earth metals, glyceryl peroxide, benzoyl peroxide and the like. Exemplified peroxides include hydrogen peroxide, carbamide peroxide, calcium peroxide and mixtures thereof, with a few of the examples being hydrogen peroxide or a mixture of hydrogen peroxide and carbamide peroxide. The total peroxide present in the foamable whitening composition, for example, ranges from about 1% by weight to about 45% by weight of the composition, further for example from about 5% by weight to about 35% by weight of the composition. Peroxide may also be present in both components of the composition. When hydrogen peroxide is used, it may typically be provided as a 50% aqueous solution. When used alone, the amount of the hydrogen peroxide aqueous solution in the first component may range from, for example, about 2% to about 90% (1% to 45% in the absence of water), as noted above, further for example, the amount may range from about 10% to about 60% (5% to 30% in the absence of water). On the other hand, when carbamide peroxide may be used, it can be, for example, used in combination with hydrogen peroxide, though it can be used alone. When used in combination, the carbamide peroxide may generally be present in an amount from, for example, about 0% by weight to about 40% by weight, and, further for example, in an amount from about 3% to about 35% by weight. At the same time, hydrogen peroxide, generally provided as a 50% aqueous solution, may be present in an amount of from, for example, about 1% to about 30% (0.5% to 15% in the absence of water); or for a further for example, in an amount of about 5% to about 30% (2.5% to 15% in the absence of water).

Even with improved efficiencies and shorter treatment times, some patients may still experience sensitivity. Suitable desensitizing agents can include alkali nitrates such as potassium nitrate, sodium nitrate and lithium nitrate; and other potassium salts such as potassium chloride and potassium bicarbonate. Potassium nitrate may be the preferable agent used. The percent of desensitizing agent can be present up to about, for example, 5 percent by weight, or for a further example, up to about 4 percent by weight, or for an even further example, up to about 3 percent by weight.

If a two-component composition is used, the second component may also preferably include as much phosphate as possible, as the phosphate salt further acts to adjust the pH of the first component. The pH of the combined components may typically be from, for example, about 5 to about 10, or for a further example, from about 6.5 to about 8.5.

In addition, optional additives in either or both components may include emulsifiers, flavorings, coloring agents, anti-plaque agents, anti-staining compounds, excipients such as emollients, preservatives, other types of stabilizers such as antioxidants, chelating agents, tonicity modifiers (e.g. sodium chloride, manitol, sorbitol or glucose), spreading agents, pH adjusting agents and/or water soluble lubricants, e.g. propylene glycol, glycerol or polyethylene glycol. The concentration of each may easily be determined by a person skilled in the art.

Lecithin, a natural emulsifier found in soy and other plants, and gum arabic, which comes from the sap of certain species of acacia trees, can also be used as emulsifier, dispersant and/or wetting agents of the present invention.

Suitable preservatives may include benzalkonium chloride, parabens, chlorhexidine acetate, chlorhexidine gluconate, sorbic acid, potassium sorbitol, chlorbutanol and phenoxyethanol.

For increasing peroxide stability during storage, a 3% disodium EDTA may be added to the nitroxyl component. Alternatively, stability may be enhanced by storing the product in a dark, cool, dry place or refrigerated. An acidic mixture may also help to stabilize the nitroxyl.

Suitable emollients may be those used for topical applications, e.g., di-n-octyl ether, fatty alcohol polyalkylene glycol ether, 2-ethylhexyl palmitate, and isopropyl fatty acid esters. The emollient, if used, may preferably be dispersed in the same part as the stabilizer, if used.

In packaging a tooth whitening composition hereof, any convenient means may be used. For a two-component version, any convenient means for effecting the separation or isolation of the two components before use can be utilized. Note, this may encapsulating the two components in a multi-phase environment. For example, a single container can be compartmentalized so that the two components may be housed in separate compartments and may be dispensed substantially simultaneously and admixed prior to application on the teeth (see FIGS. 2 and 3, described below). Alternatively, the two components can be contained in separate containers from which the respective phases are dispensed for admixture just prior to use. The containers can also include static mixers. Exemplary packaging is disclosed in U.S. Pat. Nos. 5,819,988; 6,065,645; 6,394,314; 6,564,972 and 6,698,622, which are each incorporated herein by reference.

In one exemplary embodiment of the present invention, a two-component foaming mixture can be made, whereby the two components may be provided in separate chambers of a dual-barrel syringe. Immediately before use, the two components may be mixed together in, for example, a 1:2 to a 5:1 ratio (first component to second component) by actuating the syringe. For a further example, the gels may be mixed in a 1:1 ratio. The admixed whitening gel may be applied to the surface of the teeth directly from the syringe. Other combinations of the components are contemplated by the present invention, depending on the percentage (%) variation of ingredients present in each component.

FIG. 1 shows a possible embodiment of a delivery system suited for dispensing the present invention. It is a dual-component syringe, preferably constructed of polypropylene and comprised of a plunger 1, dual-barrel body with integrated finger rest 2, and pistons 3. A mixing syringe tip comprised of a locking outer housing 4 and integrated static mixer 5 is attached. Two complimentary oral care compositions 6 and 7 can be contained within each isolated syringe barrel. When the user is ready to use the invention, the plunger is actuated towards the direction of the tip, resulting in the compositions becoming admixed within the syringe tip/static mixer component. The resultant homogenous foaming whitener 8 is expressed out of the dispenser and is ready for use.

FIG. 2 shows a possible embodiment of a delivery system suited for dispensing the present invention. It is a dual-component dispenser pump, preferably constructed of high density polypropylene and comprised of a plunger 9, upper housing with dual-barrel inner holding chambers 10, and fit into a lower housing 11 and base 12. Air-tight septum closures 13 keep the whitening composition within the holding chambers and are displaced upwards by a vacuum created when the plunger 9 is actuated. Two complimentary oral care compositions 16 and 17 can be contained within each of the isolated holding chambers 10. When the user is ready to use the invention, the plunger 9 is actuated downwards, resulting in the compositions becoming admixed within the locking mixing tip complex 14 comprising a static mixer component 15. The resultant homogenous foaming composition 18 is expressed out of the dispenser and is ready for use.

FIG. 3 shows a possible embodiment of a delivery system suited for dispensing the present invention. It is a dual-component dispenser pump, preferably constructed of high density polypropylene and comprised of a plunger 19, upper housing with dual-barrel inner holding chambers 20, and fit into a lower housing 21 and base 22. Air-tight septum closures 23 keep the whitening composition within the holding chambers and are displaced upwards by a vacuum created when the plunger 19 is actuated. Two complimentary oral care compositions 26 and 27 can be contained within each of the isolated holding chambers 20. When the user is ready to use the invention, the plunger 19 is actuated downwards, resulting in the compositions becoming expressed out of the dispenser from separate orifices. Two adjacent ribbons of the composition can be mixed together with a paint brush or swab, causing rapid foaming of the mixture. The foam can then be applied onto teeth. For storage of any remaining product, the pump has an integrated flip top closure 25 attached to the body with hinge 24.

In addition, any of the dispensers can also be fitted with a metering device for varying the proportion of each component in the final foam. The metering device can be adjusted to produce ratios of the two components of from about 10:1 to about 1:10. The device can be in the form of a dispensing system which features a measuring mechanism that connects to two separate, interlocking bottles. In such an embodiment, by rotating the dispenser head, a precise mixing ratio of blended ingredients can be attained. Specifically, a dispenser head may include two pumps that offer varying proportions of volumetric dispensing that can be individually actuated in precise relationship to the positioning of the interior disc. This interior disc can be positioned precisely or locked into a specific ratio by rotating the dispenser head. The nozzle for metering dual dispenser pump bottle can either be a configuration in which both components are mixed with a static mixer incorporated within its tip or a two-opening configuration where the components are not mixed until application. The use of metering devices can result in improved manufacturing efficiency, as fewer concentrations need to be made and the final concentration can be easily adjusted.

EXAMPLES

Example 1

Foaming Nitrogen Oxide Tooth Whitener

Ingredients for making this exemplary composition according to the invention are set out in Table 1 below. They may be prepared as follows:

Component 1 (acidic) may be prepared by dissolving 0.8 grams of Pluronic F68 in 10 ml of water, followed by the addition of 0.5 grams of Potassium Hydroxide and 0.8 grams detergent with stirring using a lab mixer at room temperature. Then the mixture may be acidified by adding 5 milliliters of 10% nitric acid and 3 grams of tartaric acid w/stirring, at 500 rpm at room temperature. The entire solution may be diluted to 100 ml by adding 80 milliliters following examples: of a 50% Superoxol solution (50% hydrogen peroxide), followed by addition of 1 gram of Potassium Nitrate and stirred until thinned to a creamy white color. Next, 1.0 grams of Calcium Nitrate may be also added. The mixture pH may then be checked. A pH range of about 1.5 to about 2.5 may be obtained through adjusting with either a 10% nitric acid or potassium hydroxide. The entire mixture may be agitated at room temperature under vacuum for 30 minutes. The resulting acidic low-viscosity solution (>300 cps) may be poured into 50 ml compartment of the two-chamber metering pump dispenser.

Component 2 (basic) may be prepared by adding 0.10 grams of potassium hydroxide and 0.50 grams of potassium iodide to 50 milliliters of distilled water, followed by the addition of 0.8 grams of detergent and 0.8 grams of foam stabilizer with stirring using a stand mixer set at 750 rpm at room temperature until a homogenous light hydrogel may be formed. Then 38 milliliters of 1% Calcium Peroxide suspension and 2 milliliters of glycerin may be added and blended until the mixture thinned and appeared clear and smooth. Then 2 grams of sodium carbonate may be slowly added, followed by slow addition of 3 grams of sodium phosphate dihydrate, 1 gram of sodium bicarbonate and 0.10 grams of Disodium Phosphate. For one optional embodiment where photo activation may be used, 1.25 milliliters of 3.33% ferrous gluconate solution may be added while mixing at 200 rpm and then at 500 rpm. For aesthetic purposes, 1 ml of FD&C Green #2 may be also added. The pH may be checked and adjusted with Potassium Hydroxide to a pH range of 10.2 to 11.2. Finally more distilled water may be added to bring the entire solution to 100 ml. To disperse and hydrate the stabilizer, and to degas any bubble formed, this component may be agitated at room temperature under vacuum for 20 minutes. The resulting low viscosity solution (48 cps) may be poured into a second 50 ml chamber of the metering pump dispenser.

TABLE 1

FOAMING NITROGEN OXIDE TOOTH WHITENER

| Ingredient | AMT | | Available From | Purpose |
|---|---|---|---|---|
| Component 1 | | | | |
| $H_2O$ | 9.00 | mL | N/A | carrier/solvent |
| PLURONIC F68 | 0.80 | g | BASF | foamer |
| KOH | 0.50 | g | Spectrum Chemical | pH modifier |
| TYLOSE H4000* | 0.80 | g | Clariant | thickener |
| $HNO_3$ 10% | 3.00 | mL | Spectrum Chemical | source of Nitrogen Oxide radicals |
| Tartaric Acid | 1.0 | g | Spectrum Chemical | foam stabilizer |
| 50% $H_2O_2$ | 80.00 | mL | Atofina | peroxide source |
| $KNO_3$ | 1.00 | g | Spectrum Chemical | stabilizer/sensitivity reliever |
| $CaNO_3.(H_2O)_4$ | 0.50 | g | Spectrum Chemical | source of Nitrogen Oxide radicals |
| $KOH/HNO_3$ | QS to pH 2.0 | same | Spectrum Chemical | pH modifier |
| Component 2 | | | | |
| $H_2O$ | 50.00 | mL | N/A | carrier/solvent |
| KI | 0.50 | g | Spectrum Chemical | peroxide activator |
| KOH | 0.10 | g same | Spectrum Chemical | pH modifier |
| PLURONIC F68 | 0.80 | g | BASF | foamer |
| TYLOSE H4000* (Hyethyl cellulose) | 0.80 | g | Clariant | thickener |
| Glycerin | 2.00 | mL | Spectrum Chemical | humectant, carrier, viscosity modifier |
| Sodium Carbonate | 1.00 | g | Spectrum Chemical | effervescent component |
| Na Phosphate Dihydrate | 1.50 | g | Spectrum Chemical | pH buffer and phosphate source |
| Baking Soda (sodium bicarbonate) | 2.00 | g | Spectrum Chemical | effervescent component |
| $Na_2H$ Phos Monohydrate | 0.50 | g | Spectrum Chemical | pH buffer/phosphate source |
| FeGluconate | 1.25 | mL | Spectrum Chemical | Nitroxyl & peroxide photoactivator |
| FDC Green #2 | 1.0 | mL | Warner Jenkins | colorant |

The components may be filled into a metering, dual component pump dispenser. Both plungers of the dual chamber dispenser may be actuated at the same time to cause foaming. Mixing of components 1 and 2 may occur in the attached mixing tip. The foam mixture produced may be applied to teeth for 3 applications of three (3) to seven (7) minutes.

Example 2

Nitrogen Oxide Tooth Whitener Gel in Dual Barrel Syringe

Ingredients for making this exemplary composition according to the invention are set out in Table 2 below. This may be made in a similar way as Example 1, except with different ingredients, as shown in Table 2.

TABLE 2

NITROGEN OXIDE TOOTH WHITENER GEL IN DUAL BARREL SYRINGE

| Ingredient | AMT | Available From | Purpose |
|---|---|---|---|
| Component 1 | | | |
| $H_2O$ | 9.00 mL | N/A | carrier/solvent |
| XANTHAN GUM | 2.00 g | Clariant | thickener |
| $HNO_3$ 10% | 3.00 mL | Spectrum | source of Nitrogen Oxide radicals |
| 50% $H_2O_2$ | 80.00 mL | Atofina | peroxide source |
| $KNO_3$ | 1.00 g | Spectrum Chemical | stabilizer - sensitivity reliever |
| EUGENOL | 1.50 mL | Junbunzlauer | gel stabilizer - sensitivity reliever |
| MINT | 2.00 mL | S&S Flavors | flavor, scent and stabilizer |
| $CaNO_3.(H_2O)_4$ | 0.50 g | Spectrum | Source of Nitrogen Oxide radicals |
| $KOH/HNO_3$ | QS to pH 2.0 same | Spectrum Chemical | pH modifier |
| Component 2 | | | |
| $H_2O$ | 50.00 mL | N/A | carrier/solvent |
| KOH | 0.10 g same | Spectrum Chemical | pH modifier |
| Xanthan Gum | 3.0 g | Spectrum Chemical | thickener |
| Glycerin | 40.00 mL | Spectrum Chemical | humectant, carrier, viscosity modifier |
| Sodium Carbonate | 1.00 g | Spectrum Chemical | effervescent component |
| Na Phosphate | 1.50 g | Spectrum Chemical | pH buffer and phosphate source |
| Baking Soda (sodium bicarbonate) | 2.00 g | Spectrum Chemical | effervescent component |
| $Na_2H$ Phos | 0.50 g | Spectrum Chemical | pH buffer and phosphate source |
| FeGluconate | 1.25 mL | Spectrum Chemical | Nitroxyl & peroxide photoactivator |
| FDC Green #2 | 1.0 mL | Warner Jenkins | colorant |

The components may be filled into a 1:1 dual chamber syringe dispenser. Both plungers of the dual chamber dispenser may be actuated at the same time to cause mixing. Mixing of components 1 and 2 may occur in the attached mixing tip. The gel mixture produced may be applied to teeth for 3 applications of ten (10) minutes.

In a further example, the metering dial of the pump dispenser may be set so that 50% of each component was dispensed simultaneously and mixed through a nozzle containing a static mixer into a 20 ml plastic weighed boat. Both plungers of the dual chamber dispenser may be actuated at the same time to cause foaming. Mixing of components 1 and 2 may occur in the attached mixing tip. The foam produced may be filled into a measuring cylinder. The volume of the expanded effervescing foaming whiteners may be compared with traditional viscous, sticky gels. The plunger may be actuated 3-6 times for dispensing 5.0 milliliters into the weighed boat. Further mixing of both components may occur by swirling the mixture for about 5 to about 10 seconds with a small disposable dental nylon applicator brush within the plastic well. The foam produced may be poured into a measuring cylinder. The volume of the expanded foam may be measured and its collapse with time monitored. The test results for foam volume, collapse rate and pH may be such that 4 ml of each component may be used taking approximately 10 seconds to actuate the dispenser 10 times. A maximum volume of 75 ml may be obtained 3 minutes after the last discharge. After 7 minutes, the volume may have decreased to 35 ml, and after 10 minutes the volume may decrease to 20 ml. It may take 30 minutes before the foam collapses completely. The pH of the foam may be about 8.2. The amount of fluid used above may be 3 ml from each chamber (6.0 ml total), and the total number of strokes of actuator may be about 3-6. The volume expansion may go from 6 ml to 75 ml. Note, the pH may have been adjusted with Potassium Hydroxide drop wise, and/or adjusted with Citric or Tartaric Acid drop wise.

This invention for nitroxyl-based whitening stands on its own as distinct from peroxide whitening and may moreover, be used as a standard gel or liquid, or, may take advantage of the newer foaming whiteners, in one or two-component form. Distinctions are found in the understanding that nitrogen oxide free radicals may be a naturally occurring, perhaps even nature's preferred way of photo bleaching organic materials in the oceans of earth. Moreover, nitrogen free radicals may work 5-100 times better than oxygen free radicals (i.e. peroxides) for three reasons: a) Nitrogen oxide radicals are more reactive than oxygen free radicals; b) Nitrogen oxide free radicals do not combine with themselves as do approximately 99.99% of all oxygen free radicals; or c) Nitrogen free radicals can combine with oxygen free radicals to form supercharged free radicals. Indeed, Nitrogen free radical production using nitroxyl compounds, with or without transition metals and UV light may require far less light energy than do peroxides. As a further note, nitrogen oxide for use herein can be produced by nitroxyl compounds which are very stable in water or like aqueous environments.

Thus created may be several formulations including paired variants of gels and foams with and without nitrogen oxide free radicals, and those containing the NO radicals substantially typically work significantly better (P<0.05) as foaming nitroxyl containing tooth whitening systems. Further, since NO radicals work so efficiently, little if any tooth sensitivity is felt, and according hereto, nitroxyl therapy is likely to have a role in prevention of periodontal disease. It might well be that such product may also help with making gums healthier. Thus also contemplated is the idea of nitrogen oxide dentifrice and nitrogen oxide mouth rinses as a way of whitening teeth and controlling gingivitis; at least leaving open that a toothpaste and/or a mouth rinse may have effects on one or both of gingival health and tooth color.

It may further be noted that the interactivity of nitroxyl chemistry with ordinary organic bodily systems may provide further basic appreciation for the elegance of this development. For a first example, the discovery of the important regulatory role that nitrogen oxide plays in our bodies was sufficiently important to win the NOBEL PRIZE for medicine in 1998. Endogenous NO radicals are responsible for blood pressure regulation, erection potency, signaling repair mechanisms when cancer causing hydrogen peroxide radicals are detected in the body, etc. Contrasted with peroxides which are apparently cancer causing; NO radicals may very likely help in the prevention cancers caused by peroxide related radicals. Still further, nitrates and nitrites are FDA approved food additives and frequently also used for bleaching fabrics, inter alia.

The present invention provides a novel composition of matter for the purpose of more rapid and safer tooth whitening. It relies primarily on the nitrogen oxide radicals NO–, $NO_2$— and $NO_3$— to catalyze and further cause the whitening of teeth, with or without a mechanical UV light source. The radicals may ultimately cause the production of chemical intermediates, which are more efficient than those present in all other previously described systems. As such the entire whitening procedure time may be considerably shorted. Consequently the patient may be more comfortable, their safety may be enhanced by cutting down exposure time from UV radiation and their level of tooth whiteness may be significantly enhanced for any given exposure time.

In a further alternative, other organic or human tissue may be conditioned using compositions hereof. For example, melanin is an organic carbon-bonded molecule and is subject to whitening in much the same manner as organic tooth stain molecules. Darker skin pigmentation is caused by the over expression or accumulation of melanin in the skin. As a result, the application of an activated mild whitener composition, containing an oxidizing agent will work to make the skin appear whiter on a temporary basis. The resultant whitening is temporary as the epithelium and melanin are replaced on a daily basis. However to the extent that persons may want an instant temporary method of appearing cosmetically lighter, this method is one possible solution. The ability to modify the appearance of pigment content in the skin, to promote an even-looking skin tone and a more youthful appearance, is highly desired in many of the world's societies. Many people desire to modify their skin tone, to reduce aging spots, melasma, etc., or for purely cosmetic reasons. In fact, in the Far East, a lighter skin tone is desirable and is associated with higher socioeconomic status.

Therefore, the present invention, in an alternate embodiment may be used as a skin whitening composition which can be effectively used as a topical agent and which would cause rapid skin lightening. For this application, the preferred peroxygen would be benzoyl peroxide, and all other oxidizers, such as nitrogen oxide or sodium chlorite present should be preferably reduced by 50% or more in the overall composition. Furthermore, the composition of the invention described herein can be optionally combined with tyrosinase inhibitors, and/or melanin cell synthesis inhibitors, along with skin exfoliating agents, which are all useful in topically applied cosmetic skin whitening formulations described in the current art.

The above specification, examples and data provide a complete description of the compositions, active agents and use of example implementations of the presently-described technology. Although various implementations of this technology have been described above with a certain degree of particularity, or with reference to one or more individual implementations, those skilled in the art could make numerous alterations to the disclosed implementations without departing from the spirit or scope of the technology hereof. Since many implementations can be made without departing from the spirit and scope of the presently described technology, the appropriate scope resides in the claims hereinafter appended. In particular, it should be understood that the described technology may be employed independent of the particular exemplar whitening compositions and methods hereof. Other implementations are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular implementations and not limiting. Changes in detail or structure may be made without departing from the basic elements of the present technology as defined in the following claims.

Accordingly, what is claimed is:

1. A tooth-whitening composition comprising:
an effective amount of a nitrogen oxide composition comprising between about 0.2% to about 1.0% nitric acid and 0.2% to 1.0% calcium nitrate in an amount effective to generate nitrate free radicals ($NO_3$—) when applied to a user's teeth for affecting tooth color, said nitrogen oxide composition contained in one or more of a paste, gel, liquid or foam,
wherein the nitrogen oxide composition includes an effective amount of nitrate free radical generative molecules that include elemental nitrogen in the oxidation state; namely, NO3—;
wherein the nitrate free radical generative molecules are present in effective amounts to convert from the initial nitrogen oxide composition state to generate and release, when in contact with one or more teeth, NO3— free radicals in sufficient amounts to reduce on said one or more teeth enamel chromophores into less colored and/or colorless moieties.

2. A composition according to claim 1 contained in one or more of a dentifrice, mouth rinse, tooth paste, tooth gel, or oral foam.

3. A composition according to claim 1 contained in one or more oral care formats of a liquid oral care format, a paste oral care format, a gel oral care format or a foam oral care format.

4. A composition according to claim 1 wherein the composition includes nitrate and/or nitrite ions.

5. A composition according to claim 1 wherein the composition includes nitrogen oxide free radical generative molecules that include one or more of nitrosonium cation (NO+) and nitrogen oxide free radical anion (NO–).

6. A composition according to claim 1 wherein the composition includes a nitrogen oxide free radical generative compound that includes any molecule that contains a terminal group of nitrogen and oxygen.

7. A composition according to claim 1 wherein the composition is provided in one of a single phase or multiple phase forms.

* * * * *